(12) United States Patent
Singh et al.

(10) Patent No.: US 6,492,566 B1
(45) Date of Patent: Dec. 10, 2002

(54) PROCESS FOR THE PREPARATION OF DIHYDROXYDIPHENYLMETHANES

(75) Inventors: Anand Pal Singh, Pune (IN); Sharda Dagade, Pune (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 09/487,426

(22) Filed: Jan. 19, 2000

(30) Foreign Application Priority Data

Feb. 25, 1999 (IN) .......................................... 333/DEL/99

(51) Int. Cl.[7] .............................................. C07C 39/12
(52) U.S. Cl. ...................................................... 568/727
(58) Field of Search ................................. 568/727, 728

(56) References Cited

U.S. PATENT DOCUMENTS

| | | | | |
|---|---|---|---|---|
| 3,496,239 A | * | 2/1970 | Hamilton | 568/727 |
| 3,728,408 A | * | 4/1973 | Tabias | 568/727 |
| 4,306,106 A | * | 12/1981 | Kerr | 568/727 |
| 4,895,988 A | * | 1/1990 | Clerici | 568/727 |

* cited by examiner

*Primary Examiner*—Michael L. Shippen
(74) *Attorney, Agent, or Firm*—Ladas & Parry

(57) ABSTRACT

The present invention discloses an improved process for the preparation of dihydroxydiphenylmethanes by reacting phenol over a microporous alumino-silicate zeolite catalyst composite material in the presence of a condensing agent and a solvent at a temperature in the range of 5 to 200° C. for a period between 0.1 to 24 hours at autogeneous pressure and separating the dihydroxydiphenylmethanes by any conventional method.

8 Claims, No Drawings

PROCESS FOR THE PREPARATION OF DIHYDROXYDIPHENYLMETHANES

FIELD OF THE INVENTION

The present invention relates to an improved process for the preparation of dihydroxydiphenylmethanes. More particularly, the present invention relates to a process for the selective preparation of 4,4'-dihydroxydiphenylmethane by reacting phenol with formaldehyde in the presence of microporous zeolite catalyst.

BACKGROUND OF THE INVENTION 4,4'-dihydroxydiphenylmethane is useful as a starting material for the production of polycarbonate resins, polyester resins and epoxy resins and as a modifier and stabiliser for phenol resins.

Several methods are known in the art for the production of dihydroxydiphenylmethanes. Japanese Patent Jpn. Kokai Tokkyo Koho JP 0687775 (CA 121:57131) discloses a method for the condensation of phenol with aqueous formaldehyde using phosphotungstic acid which consists of 10:43:47 ratio of 2,2'-, 2,4'- and 4,4'-dihydroxydiphenylmethane isomers. EP 331, 172: CA 112:7160 discloses a method for reacting phenol with formaldehyde in the presence of an activated clay at 80° C. for 2 hours to give 38.8% of 4,4'-, 15.8% of 2,2'-, and 38.4% of 2,4'-dihydroxydiphenylmethane and 7.0% oligomer JP 63, 238, 632: CA 116: 75045 discloses a method for reacting phenol with formaldehyde in the presence of activated clay catalyst to give 2,2'-, 2,4'-, and 4,4'dihydroxydiphenylmethane in the ratio of 17.1: 41.4:44.5.

U.S. Pat. No. 4,400,554: CA 99:175378 discloses a method for reacting phenol with formaldehyde in a two phase mixture in the presence of aqueous $H_3PO_4$ at 45° C. to give 4,4'-, 2,4'- and 2,2'-dihydroxydiphenylmethane in a ratio of 55:37:8. U.S. Pat. No. 4,937,392 (1990) discloses a process for reacting phenol with formaldehyde in the presence of activated clay at 80° C. under nitrogen atmosphere for two hours to give 4,4'-, 2,4'- and 2,2'-dihydroxydiphenylmethane in a ratio of 42.8:40.5:16.7. JP-B-39-26844 discloses a method for reacting phenol with formaldehyde in the presence of urea. U.S. Pat. No. 2,617, 832 discloses a process for reacting phenol with dimethylol urea in the presence of an acidic catalyst.

A number of methods are known in the prior art for preparing dihydroxydiphenylmethane by reacting phenol with formaldehyde. Examples thereof include a method wherein an inorganic liquid acid such as hydrochloric acid, sulphuric acid or phosphoric acid is used as catalysts (cf. JP-A-58-177928; the term JP-A- as used herein refers to unexamined published Japanese patent applications. Also, cf. British patent No. 1,493,759 and U.S. Pat. No. 2,792, 429).

However, the above methods have several disadvantages from the industrial point of view since the selectivity for 4,4'-dihydroxydiphenylmethane is low in each case. The catalyst is also homogeneous in some cases. Thus, a large amount of base is required to. neutralise the homogeneous acid catalysts causing problems in respect of the disposal of the resulting salts.

In view of the above-mentioned problems of homogeneous catalysts and low selectivity for 4,4'dihydroxydiphenylmethane in the prior art processes, it was felt necessary to develop an improved process for the production of dihydroxydiphenylmethanes and particularly 4,4'dihydroxydiphenylmethane with high selectivity from the condensation of phenol with formaldehyde which process does not have the disadvantages encountered by the prior art processes.

OBJECTS OF THE INVENTION

It is an object of the present invention to solve the above-mentioned problems by establishing a process for the advantageous preparation of dihydroxydiphenylmethane and particularly 4,4'-dihydroxydiphenylmethane in high selectivity.

It is another object of the invention to provide a process for the preparation of dihydroxydiphenylmethane and particularly 4,4'-dihydroxydiphenylmethane in high selectivity that allows recycling of the catalyst.

It is another object of the invention to provide a process for the preparation of dihydroxydiphenylmethane and particularly 4,4'-dihydroxydiphenylmethane in high selectivity that does not require disposal of inorganic byproducts.

SUMMARY OF THE INVENTION

The above and other objects of the present invention are achieved by the present invention in a novel manner by carrying out the condensation of phenol with a condensation agent, preferably formaldehyde in the presence of an inert solvent over a solid catalyst composite material aluminosilicate zeolite catalyst. Ideally, the zeolite catalyst is a microporous alumino-silicate zeolite catalyst composite and the reaction is carried out at a temperature of from 5 to 200° C. The reaction is equally effective with other condensing agents as well.

Accordingly, the present invention relates to an improved process for the preparation of dihydroxydiphenylmethanes which comprises reacting phenol over a microporous alumino-silicate zeolite catalyst composite material in the presence of a condensing agent and a solvent at a temperature in the range of 5 to 200° C. for a period between 0.1 to 24 hours at autogeneous pressure and separating the dihydroxydiphenylmethanes by any conventional method.

In one embodiment of the invention, the condensing agent is selected from the group comprising aqueous formaldehyde, paraformaldehyde and trioxane, the aqueous formaldehyde being most preferred.

In another embodiment of the invention, the solvent used is selected from the group comprising 1,2-dichloroethane, chloroform, $CCl_4$, benzonitrile, nitrobenzene, acetonitrile, 1,2-dichlorobenzene or methylethylketone or mixtures thereof In a further embodiment of the invention the zeolite catalyst composite material is selected from the group comprising zeolite H-beta, H-ZSM5, H-ZSM12, H-mordenite, H-Y, RE-Y and MCM-22.

In another embodiment of the invention, the ratio of the phenol to condensing agent is in the range between 5:1 to 10:1.

In one embodiment of the invention, wherein the zeolite and the phenol may be combined prior to reacting, added simultaneously at the time of the reaction.

In another embodiment of the invention, the zeolite and/or phenol are suspended in a solvent prior to addition to the condensing agent.

In one embodiment of the invention, the solvent used is selected from the group comprising of alcohol, aromatic or aliphatic hydrocarbons, ketones, chloroaromatic or nitroaromatic compounds, preferably methylethylketone.

In another embodiment of the invention, it is possible to selectively and efficiently prepare 4,4'-dihydroxydiphenylmethane while separating the ortho and the meta position products.

In another embodiment of the invention, the reaction may preferably be carried out at a relatively low temperature in the range of 20 to 200° C.

DETAILED DESCRIPTION OF THE INVENTION

The process of the invention is suitable as an industrial process for the production of 4,4'-dihydroxydiphenylmethane in high selectivity due to the use of non-hazardous solid aluminosilicate catalysts and the absence of any risk of explosion. The reactants and solvents that are used in the process of the present invention must be of high purity.

In the present invention, zeolite may be added to the reactant by different methods:

1. The zeolite and the phenol may be combined and added to the condensing agent prior to the reaction.
2. The zeolite and the phenol may be added simultaneously to the reaction system at the time of the reaction.
3. The zeolite may be suspended in a solvent, and a predetermined amount of phenol and the condensing agent being added thereto.
4. The zeolite may be suspended in the phenol and solvent, and a predetermined amount of condensing agent being added thereto.

Preferably, the catalyst composite material used is a microporous aluminosilicate zeolite H-beta type. The proportion of phenol to formaldehyde ratio, solvent and H-beta used ranges between 5:1 to 10:1 molar ratio and 0 to 50 ml and 0.01 to 100 g/mol phenol respectively.

The present invention will now be described with reference to the accompanying examples, which are merely illustrative and should not be construed as limiting the scope of the invention in any manner.

EXAMPLE 1

This example illustrates the procedure for the condensation of phenol with aqueous formaldehyde to 4,4'-dihydroxydiphenylmethane, 2,4'-dihydroxydiphenylmethane and 2,2'-dihydroxydiphenylmethane. The reaction was carried out in an autoclave. 188 g (2 mol) of phenol was reacted with 32.4 g (0.4 mol) formaldehyde (37%) in the presence of 1 g of activated catalyst composite material zeolite H-beta at 80° C. for three hours. After completion of the reaction, the reaction mixture was cooled to room temperature and the catalyst filtered off. The reaction mixture thus obtained was analysed by gas chromatography. The results are listed in Table 1.

TABLE 1

Condensation of phenol with aqueous formaldehyde over catalyst composite material aluminosilicate zeolite H-beta after three hours.

| | |
|---|---|
| Conversion of phenol (wt %) | 20.6 |
| Product distribution (wt %) | |
| 4,4'-dihydroxydiphenylmethane | 34.5 |
| 2,4'-dihydroxydiphenylmethane | 49.0 |
| 2,2'-dihydroxydiphenylmethane | 15.5 |
| Others | 1.0 |

EXAMPLE 2

This example illustrates the procedure for the condensation of phenol with aqueous formaldehyde to 4,4'-dihydroxydiphenylmethane, 2,4'-dihydroxydiphenylmethane and 2,2'-dihydroxydiphenylmethane. 94 g (1 mol) of phenol was reacted with 16.2 g (0.2 mol) formaldehyde (37%) in the presence of 2 g of catalyst composite material zeolite H-ZSM5 at 80° C. for three hours under stirring in an autoclave. After completion of the reaction, the reaction mixture was cooled to room temperature, filtered off and analysed by gas chromatography. The results are listed in Table 2.

TABLE 2

Condensation of phenol with aqueous formaldehyde over catalyst composite material aluminosilicate zeolite H-ZSM5 after three hours.

| | |
|---|---|
| Conversion of phenol (wt %) | 16.7 |
| Product distribution (wt %) | |
| 4,4'-dihydroxydiphenylmethane | 26.8 |
| 2,4'-dihydroxydiphenylmethane | 46.3 |
| 2,2'-dihydroxydiphenylmethane | 25.0 |
| Others | 1.9 |

EXAMPLE 3

This example illustrates the procedure for the condensation of phenol with aqueous formaldehyde to 4,4'-dihydroxydiphenylmethane, 2,4'-dihydroxydiphenylmethane and 2,2'-dihydroxydiphenylmethane. 47 g (0.5 mol) of phenol was reacted with 8.1 g (0.9 mol) formaldehyde (37%) in the presence of 3 g of catalyst composite zeolite material H-mordenite at 80° C. for three hours under stirring in an autoclave. After completion of the reaction, the reaction mixture was cooled to room temperature, filtered off and analysed by gas chromatography. The results are listed in Table 3.

TABLE 3

Condensation of phenol with aqueous formaldehyde over catalyst composite material aluminosilicate zeolite H-mordenite after three hours.

| | |
|---|---|
| Conversion of phenol (wt %) | 17.9 |
| Product distribution (wt %) | |
| 4,4'-dihydroxydiphenylmethane | 26.6 |
| 2,4'-dihydroxydiphenylmethane | 47.3 |
| 2,2'-dihydroxydiphenylmethane | 24.3 |
| Others | 1.8 |

EXAMPLE 4

This example illustrates the procedure for the condensation of phenol with aqueous formaldehyde to 4,4'- dihydroxydiphenylmethane, 2,4'-dihydroxydiphenylmethane and 2,2'-dihydroxydiphenylmethane. 470 g (5 mol) of phenol was reacted with 81 g (1 mol) formaldehyde (37%) in the presence of 5 g of activated catalyst composite material zeolite H-Y at 80° C. for three hours under stirring in an autoclave. After the reaction, the reaction mixture was cooled to room temperature, filtered off and analysed by gas chromatography. The results are listed in Table 4.

TABLE 4

Condensation of phenol with aqueous formaldehyde over catalyst composite material aluminosilicate zeolite H-Y after three hours.

| | |
|---|---|
| Conversion of phenol (wt %) | 14.4 |
| Product distribution (wt %) | |
| 4,4'-dihydroxydiphenylmethane | 13.1 |
| 2,4'-dihydroxydiphenylmethane | 52.2 |
| 2,2'-dihydroxydiphenylmethane | 33.0 |
| Others | 1.7 |

EXAMPLE 5

This example illustrates the procedure for the condensation of phenol with aqueous formaldehyde to 4,4'-dihydroxydiphenylmethane, 2,4'-dihydroxydiphenylmethane and 2,2'-dihydroxydiphenylmethane. 940 g (10 mol) of phenol was reacted with 162 g (2 mol) formaldehyde (37%) in the presence of 10 g of activated catalyst composite zeolite material MCM-22 at 80° C. for three hours under stirring in an autoclave. After completion of the reaction, the reaction mixture was cooled to room temperature, filtered off and analysed by gas chromatography. The results are listed in Table 5.

TABLE 5

Condensation of phenol with aqueous formaldehyde over catalyst composite material aluminosilicate zeolite MCM-22 after three hours.

| | |
|---|---|
| Conversion of phenol (wt %) | 22.5 |
| Product distribution (wt %) | |
| 4,4'-dihydroxydiphenylmethane | 24.4 |
| 2,4'-dihydroxydiphenylmethane | 53.7 |
| 2,2'-dihydroxydiphenylmethane | 21.1 |
| Others | 0.8 |

EXAMPLE 6

This example illustrates the effect of solvent (methyl ethyl ketone) on the conversion of phenol with aqueous formaldehyde and selectivity for 4,4'-dihydroxydiphenylmethane among 4,4'-dihydroxydiphenylmethane, 2,4'-dihydroxydiphenylmethane and 2,2'-dihydroxydiphenylmethane. 940 g (10 mol) of phenol was reacted with 162 g (2 mol) formaldehyde (37%) in the presence of 200 ml solvent (methyl ethyl ketone) over 5 g of activated catalyst composite zeolite H-beta at 80° C. for three hours under stirring in an autoclave. After completion of the reaction, the reaction mixture was cooled to room temperature and analysed by gas chromatography. The results are listed in Table 6.

TABLE 6

Condensation of phenol with aqueous formaldehyde in the presence of methyl ethyl ketone over catalyst composite material aluminosilicate zeolite H-beta for three hours.

| | |
|---|---|
| Conversion of phenol (wt %) | 12.9 |
| Product distribution (wt %) | |
| 4,4'-dihydroxydiphenylmethane | 53.5 |
| 2,4'-dihydroxydiphenylmethane | 35.5 |
| 2,2'-dihydroxydiphenylmethane | 1.9 |
| Others | 9.1 |

EXAMPLE 7

This example describes the effect of the condensing agent in the reaction of phenol with paraformaldehyde on the conversion of phenol and selectivity for 4,4'-dihydroxydiphenylmethane among 4,4'-dihydroxydiphenylmethane, 2,4'-dihydroxydiphenylmethane and 2,2'-dihydroxydiphenylmethane. 30 g (0.32 mol) of phenol was reacted with 20 g paraformaldehyde in the presence of 150 ml methyl ethyl ketone over 6 g of activated catalyst composite zeolite H-beta at 80° C. for three hours under stirring in an autoclave. After completion of the reaction, the reaction mixture was cooled to room temperature and analysed by gas chromatography. The results are listed in Table 7.

TABLE 7

Effect of condensing agent (paraformaldehyde) in the condensation of phenol over catalyst composite material aluminosilicate zeolite H-beta in the presence of methyl ethyl ketone after three hours.

| | |
|---|---|
| Conversion of phenol (wt %) | 5.3 |
| Product distribution (wt %) | |
| 4,4'-dihydroxydiphenylmethane | 53.0 |
| 2,4'-dihydroxydiphenylmethane | 26.5 |
| 2,2'-dihydroxydiphenylmethane | 4.3 |
| Others | 16.2 |

EXAMPLE 8

This example describes the effect of the condensing agent in the reaction of phenol with trioxane on the conversion of phenol and selectivity for 4,4'-dihydroxydiphenylmethane among 4,4'-dihydroxydiphenylmethane, 2,4'-dihydroxydiphenylmethane and 2,2'-dihydroxydiphenylmethane. 94 g (1 mol) of phenol was reacted with 90 g of trioxane in the presence of 200 ml methyl ethyl ketone over 30 g of catalyst composite zeolite H-beta at 80° C. for three hours under stirring in an autoclave. After completion of the reaction, the reaction mixture was cooled to room temperature and analysed by gas chromatography. The results are listed in Table 8.

TABLE 8

Effect of condensing agent (trioxane) in the condensation of phenol over catalyst composite material aluminosilicate zeolite H-beta in the presence of methyl ethyl ketone.

| | |
|---|---|
| Conversion of phenol (wt %) | 9.5 |
| Product distribution (wt %) | |
| 4,4'-dihydroxydiphenylmethane | 56.4 |
| 2,4'-dihydroxydiphenylmethane | 26.6 |

TABLE 8-continued

Effect of condensing agent (trioxane) in the condensation of phenol over catalyst composite material aluminosilicate zeolite H-beta in the presence of methyl ethyl ketone.

| | |
|---|---|
| 2,2'-dihydroxydiphenylmethane | 2.5 |
| Others | 14.5 |

The advantages of the present invention are:
1. A corrosion free plant can be used.
2. A recyclable zeolite catalyst can be used.
3. The problem of disposal of inorganic byproducts does not arise.
4. Due to the shape, selectivity and porous structure of the zeolites and the presence of the solvent, these catalysts produce higher amounts of 4,4'-dihydroxydiphenylmethane at the expense of other isomers and higher oligomers.
5. The starting materials are easily available and easy to handle rendering the process of the invention with greater merit for industrial application.

We claim:

1. An improved process for the preparation of dihydroxydiphenylmethanes which comprises reacting phenol over a microporous alumino-silicate zeolite catalyst composite material selected from the group consisting of zeolite H-beta, H-SM12 and MCM-22, in the presence of a condensing agent wherein the condensing agent is selected from the group consisting of aqueous formaldehyde, paraformaldehyde and trioxane and a solvent selected from the group consisting of alcohol, aromatic or aliphatic hydrocarbons, ketones, chloroaromatic and nitroaromatic compounds at a temperature in the range of 5 to 200° C. for a period between 0.1 to 24 hours at autogeneous pressure and separating the dihydroxydiphenylmethanes by any conventional method.

2. A process as claimed in claim 1 wherein the solvent is selected from the group consisting of 1,2-dichloroethane, chloroform, $CCl_4$, benzonitrile, nitrobenzene, acetonitrile, 1,2-dichlorobenzene, methylethylketone and mixtures thereof.

3. A process as claimed in claim 1 wherein the molar ratio of the phenol to the condensing agent is in the range of from 5:1 to 10:1.

4. A process as claimed in claim 1 wherein the zeolite and the phenol are combined prior to reacting and added simultaneously at the time of the reaction.

5. A process as claimed in claim 1 wherein the zeolite and/or phenol are suspended in a solvent prior to addition to the condensing agent.

6. A process as claimed in claim 1 wherein the ortho and the meta position products are separated.

7. A process as claimed in claim 1 wherein the reaction is carried out at temperature in the range of 20 to 200° C.

8. The process according to claim 3, wherein the solvent is methylethylketone.

* * * * *